United States Patent
Niggl et al.

(10) Patent No.: US 9,551,615 B2
(45) Date of Patent: Jan. 24, 2017

(54) MONOCHROMATOR COMPRISING VIBRATION RESISTANT MOVEABLE OPTICAL ELEMENTS

(71) Applicant: TECAN Trading AG, Mannedorf (CH)

(72) Inventors: Lutz Niggl, Waging (DE); Andreas Steinbacher, Grodig (AT)

(73) Assignee: TECAN TRADING AG, Mannedorf (CH)

( * ) Notice: Subject to any disclaimer, the term of this patent is extended or adjusted under 35 U.S.C. 154(b) by 14 days.

(21) Appl. No.: 14/732,170

(22) Filed: Jun. 5, 2015

(65) Prior Publication Data

US 2016/0018261 A1  Jan. 21, 2016

(30) Foreign Application Priority Data

Jul. 18, 2014 (CH) ........................................ 1093/14

(51) Int. Cl.
| | |
|---|---|
| *G01J 3/12* | (2006.01) |
| *G01J 3/18* | (2006.01) |
| *G01J 3/06* | (2006.01) |
| *G01N 21/25* | (2006.01) |
| *G01N 21/64* | (2006.01) |

(52) U.S. Cl.
CPC .. *G01J 3/18* (2013.01); *G01J 3/06* (2013.01); *G01N 21/255* (2013.01); *G01N 21/64* (2013.01); *G01J 2003/062* (2013.01); *G01N 2201/0635* (2013.01)

(58) Field of Classification Search
CPC ............ G21K 1/06; G21K 1/067; G21K 1/00; G01J 2003/1866

USPC ......................................................... 356/331
See application file for complete search history.

(56) References Cited

U.S. PATENT DOCUMENTS

| | | | | |
|---|---|---|---|---|
| 4,804,266 A | * | 2/1989 | Barshad | G01J 3/06 356/308 |
| 5,359,409 A | * | 10/1994 | Wildnauer | G01J 3/18 356/328 |

(Continued)

FOREIGN PATENT DOCUMENTS

| | | |
|---|---|---|
| DE | 59311 A | 12/1967 |
| EP | 1498707 B1 | 11/2009 |
| GB | 2216601 A | 10/1989 |

OTHER PUBLICATIONS

European Office Action of corresponding European Patent Application No. 15166308-5, dated Sep. 21, 2016.

*Primary Examiner* — Yara B Green
(74) *Attorney, Agent, or Firm* — Notaro, Michalos & Zaccaria P.C.

(57) ABSTRACT

A monochromator has at least one optical grating which is rotatable in relation to incident light of a source of light, a drive unit to rotate the optical grating by a connected drive rod around a longitudinal axis, and a control unit to control the drive unit and thereby the rotation of the optical grating. The drive unit further has a first damping element with at least one electrical conductive surface, and a second damping element which provides at least one magnetic field having a magnetic axis which penetrates the electrical conductive surface. One of the first and second damping elements is fixed to the drive rod and is rotatable along with the drive rod around the longitudinal axis thereof in relation to the other one of the second or first damping element.

20 Claims, 4 Drawing Sheets

(56) References Cited

U.S. PATENT DOCUMENTS

| | | | | |
|---|---|---|---|---|
| 5,497,230 A | * | 3/1996 | Ohkubo | G01J 3/28 356/328 |
| 6,587,196 B1 | * | 7/2003 | Stippick | G01J 3/06 356/308 |
| 6,678,044 B2 | * | 1/2004 | Kaneko | G01J 3/02 356/331 |
| 6,710,332 B2 | * | 3/2004 | Joukawa | G01D 5/34715 250/226 |
| 6,853,450 B1 | * | 2/2005 | Iwasaki | G01J 3/02 356/334 |
| 6,973,233 B1 | * | 12/2005 | Tomita | G01J 3/10 356/334 |
| 2004/0033072 A1 | * | 2/2004 | Kaneko | G01J 3/1804 398/34 |
| 2005/0017191 A1 | | 1/2005 | Montagu et al. | |
| 2006/0176480 A1 | * | 8/2006 | Toth | G01J 3/02 356/328 |
| 2009/0225315 A1 | | 9/2009 | Wilt et al. | |

\* cited by examiner

MONOCHROMATOR COMPRISING VIBRATION RESISTANT MOVEABLE OPTICAL ELEMENTS

RELATED PATENT APPLICATIONS

This patent application claims priority of the Swiss patent application No. CH 01093/14 filed on Jul. 18, 2014, the entire content of which is incorporated herein by explicit reference.

RELATED FIELD OF TECHNOLOGY

The present invention relates to a monochromator comprising at least one optical grating in which incident light of a light source is fanned-out (De: Auffächern) continuously, according to the preamble of the independent claim 1. Said optical grating is configured rotatable in order to allow alignment thereof in relation to incident light. Further, the monochromator comprises a drive unit for rotating the optical grating, as well as a drive rod for connecting the drive unit to the optical grating in order to allow rotation of the optical grating. In doing so, the drive rod has a longitudinal axis, wherein the drive rod and the optical grating are rotatable around thereof. Further, the monochromator comprises a control unit for controlling the drive unit and hence the rotation of the optical grating.

Further, the present invention relates to a usage of a monochromator and a system for measuring fluorescence and/or luminescence and/or absorption of samples irradiated by light from a light source, wherein the system comprises at least one monochromator.

RELATED PRIOR ART

In many cases, particularly in biological or clinical laboratories, optical equipment is deployed to analyze liquid or solid samples. Having regard to the respective employment, different devices are dedicated: Photometers are used to measure a light transmitted through a liquid sample. For example, photometers are used to determine concentration of DNA. Nephelometers are used to detect light scattered from a sample, in order to determine concentration of a suspension of small particles inside a liquid, for example. In contrast, a fluorometer is used to measure fluorescence emitted from a sample. Additionally, said devices can be configured such that the wavelength of excitation light and/or the wavelength of light emitted from the sample can be selected selectively. Measuring systems combining a plurality of such devices are referred to as multifunctional readers. For example, assuming such multifunctional readers are specifically configured to analyze samples in wells of so called microtiter plates, a variety of samples can be analyzed optically for different applications.

In recent years, more frequently, such multifunctional readers are utilized in different laboratories due to compactness and versatility thereof. For example, in order to allow spectral separation and isolation of particular wavelengths from incident polychromatic light (i.e. light composed of different wavelengths), monochromators are utilized in said multifunctional readers. Such monochromator can fan-out incident light by means of a prism, for example. Alternatively, a monochromator can comprise an optical grating used to deflect and hence fan-out incident light. For analysis, only the desired wavelength range is passed by means of a slit diaphragm disposed downstream. A multifunctional reader comprising a monochromator is known from patent document EP 1 498 707 B1, for example.

In order to allow continuously fanning-out of polychromatic light, for example, said light is directed to the optical grating. The different wavelengths of the polychromatic light are refracted on the special grating-like coating in different magnitudes, resulting to the addressed fan-out. By means of a slit diaphragm disposed downstream, a desired wavelength can be read-out from the fanned-out light beam in a local dependent manner. Selection of the desired wavelength is performed by moving the optical grating, since the slit diaphragm disposed downstream is typically mounted fixedly.

Depending on the orientation of the optical grating in relation to the incident light, a selected wavelength of the light, which is fanned-out wavelength selective, impinges the filter in a local dependent manner. Therefore, the wavelength selection is performed by means of positioning the optical grating in relation to the incident light.

In order to allow orientation of the optical grating in relation to the incident light, in as much as possible continuously variable fashion, different drive systems are employed. Usage of a step motor is known, used to directly rotate the optical grating around an axis by means of a drive rod. Such step motor allows rapid and discrete rotational movement of the optical grating, which is in particular advantageously for the so called "High Speed Continuous Wavelength Scanning" or rather which renders thereof possible. However, in case of different orientations or rather rotation angles of the optical grating are changed rapidly—which rapid changes produce increased acceleration forces and deceleration forces—inertia, in particular inertia of the optical grating, results in high frequently mechanical vibrations of the optical grating. In order to obtain desired wavelength precision, this results in prolonged waiting time periods, during which said vibrations decay and finally only the desired wavelength impinges the slit diaphragm disposed downstream.

It is known to utilize mechanical damping elements, in particular viscosity damper in order to damp said vibrations. These damper realize a strong damping action, in particular in case of high frequency resonances, but however are less efficient in case of vibrations occurring upon stop of movement, for example. As a further disadvantage, the optical grating which is to be rotated, does not, within a predetermined range of angles, for example a discrete range of angles of a step motor, always stop in a targeted centered angle position due to said damping, but rather in most cases stops in an off-centered angle position. Therefore, the optical grating stops in an angle position which is undetermined within said range of angles, resulting to a non-precise positioning. This results in a non-precise wavelength selection.

In the field of monochromators, efforts are made aiming to realize an optical grating which rotates substantially free of frictional losses, in order to achieve positioning in high velocity and high precision. These efforts comprise usage of high precision ball-bearings for pivotal bearing of said optical grating free of frictional losses, as well as usage of high quality step motors, which are substantially free of frictional losses. In doing so, as a whole, influences introduced by said ball-bearing and said step motor are reduced to an absolute minimum. However, the provision of the mechanical damping disadvantageously counteracts said efforts.

A further disadvantage in using of a mechanical damping element in a monochromator is in the wear caused by friction. Precision of the positioning additionally degrades if wear increases.

OBJECT AND SUMMARY OF THE PRESENT INVENTION

It is therefore object of the present invention to propose a monochromator allowing to perform spectral measurements with different wavelengths to be read-out, with high precision and within short waiting time periods.

This object is achieved by means of the features of independent claim 1.

Further preferred and inventive features are provided in the respective dependent claims.

Advantages of the present invention comprise the following:

A transition between different selected wavelengths, which are used to perform spectral analysis, can be performed quickly and free of prolonged waiting time periods, without suffering drawbacks in view of the precision of the selected wavelength.

The contact-free movement of elements of the eddy current damping results in a non-wear damping of oscillations or rather vibrations caused by the movement of the optical grating.

The applied damping force is proportional to the rotational speed of the optical grating.

BRIEF INTRODUCTION OF THE ATTACHED DRAWINGS

In the following, the present invention will be shown in more detail by reference to schematic diagrams accompanying this application. These diagrams shall document selected embodiments of the invention, which do not limit the scope of the present invention. It is shown in:

FIGS. 1A and 1B show an overview of optical paths conveyed by an monochromator according to the invention, wherein essentially optical elements are shown, wherein:
FIGS. 3A and 3B show different shapes of the electrical conductive disc of the monochromator, wherein:
FIGS. 4A to 4G show different layouts and arrangements between the first damping element comprising an electrical conductive face and the second damping element comprising a magnetic field, in relation to each other, wherein:
FIGS. 5A and 5B show a comparison between transient oscillations of the optical grating of a monochromator at a selected wavelength, wherein the setting time is depicted based on the measurable wavelength offset, wherein:
FIGS. 6A and 6B show an exemplary structure of the inventive monochromator, wherein.

DETAILED DESCRIPTION OF THE PRESENT INVENTION

Figure 1A:
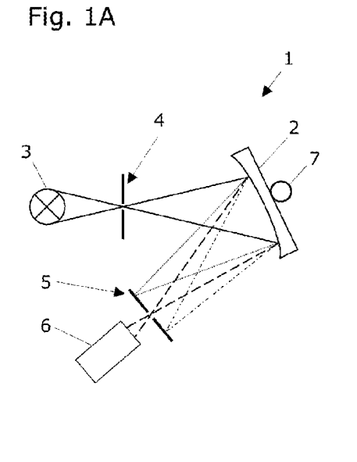
FIG. 1A: shows a monochromator having a single optical grating.
Figure 1B:
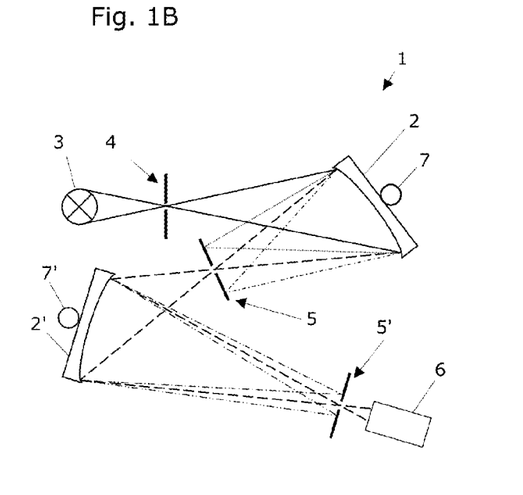
FIG. 1B: shows a dual-monochromator comprising two optical gratings.

FIGS. 1A and 1B show in an overview light paths conveyed by means of a monochromator 1 according to the present invention including essential optical means. In FIG. 1A the monochromator 1 is shown having only one optical grating 2. The light ray of a light source 3 passes through a first slit diaphragm 4 and impinges the optical grating 2. The incident light ray is deflected by means of the optical grating 2 resulting to be fanned-out continuously. The fanned-out light impinges a first downstream slit diaphragm 5, which only passes a desired range of wavelengths. The first downstream slit diaphragm 5 is mounted fixedly. In other words, a desired wavelength is read-out from the fanned-out light ray in a local dependent manner. The light comprising the read-out range of wavelengths impinges a downstream analysis apparatus 6. Exemplary ranges of wavelengths are shown in dotted lines or rather chain dotted lines, wherein the light thereof does not pass the first downstream slit diaphragm 5.

In order to select the desired wavelength at the first downstream slit diaphragm 5, the optical grating 2 is rotated. A selected wavelength of the light fanned-out corresponding to respective wavelengths impinges the filter in a local dependent manner corresponding to the orientation of the optical grating 2 in relation to the incident light. Hence, selection of the wavelength is performed by means of positioning the optical grating 2 in relation to the incident light. In doing so, the optical grating 2 is rotated by means of a drive rod 7 of a drive unit to be described later, which drive rod 7 is fixed to the optical grating 2.

FIG. 1B shows a composition of a light path conveyed by means of the monochromator 1 according to the composition in FIG. 1A as described above, wherein a further optical grating 2' is disposed downstream of the first downstream slit diaphragm 5 in the shown installation. A light which impinges the second optical grating 2' is deflected and fanned-out continuously by means of the second optical grating 2' as well. The light fanned-out in such a way impinges a second downstream slit diaphragm 5', which in turn only passes a desired range of wavelengths. Hence, the desired wavelength is read-out from the fanned-out light ray in a local dependent manner, which desired wavelength impinges the downstream analysis apparatus 6. The second downstream slit diaphragm 5' is mounted fixedly as well, while the second optical grating 2' is rotatable in order to accomplish a precise selection of the range of wavelengths. In order to accomplish rotation of the second optical grating 2', the second optical grating 2' is connected to a second drive rod 7', which is rotated by means of a drive unit (not shown).

Figure 2:
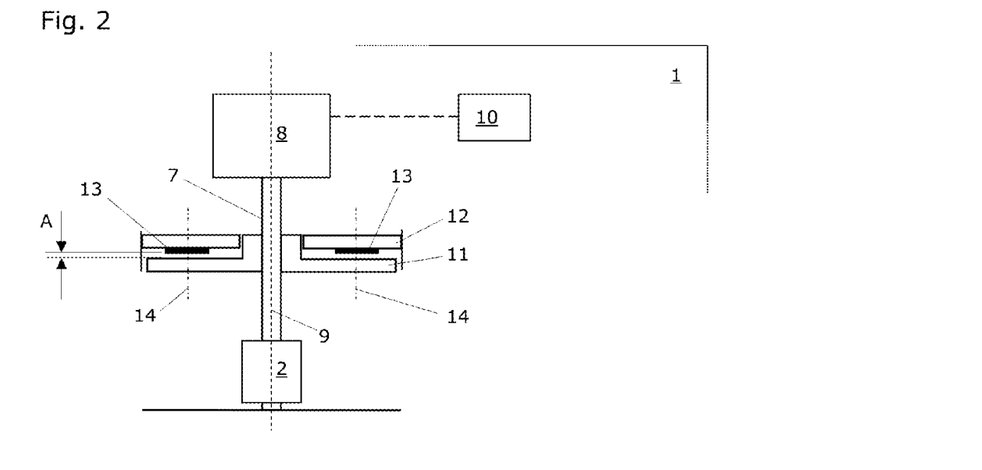
FIG. 2 shows a front view of a monochromator according to the invention in a schematic view, depicting essential elements of the drive and the damping.

FIG. 2 shows a schematic front view of an inventive monochromator 1 having essential elements of the drive and the damping. The inventive monochromator 1 comprises a drive unit 8 for rotation of the optical grating 2 via the interposed drive rod 7 (also refer to FIG. 1A). The drive rod 7, which projects from the drive unit 8 is connected to the optical grating 2 fixedly, i.e. in a torsionally rigid manner. The drive rod 7 extends along a longitudinal axis 9, wherein the drive rod 7 and the optical grating 2 are rotatable around thereof. In order to accomplish precise rotational control, the drive unit 8 is controlled by means of a control unit 10.

The drive unit 8 comprises a step motor. A step motor achieves to rapidly rotate the optical grating 2 within discrete ranges of angles. The drive rod 7 is connected to an electrical conductive disc 11 (the first damping element) in a torsionally rigid manner. Preferably, in doing so, the drive rod 7 extends through the center (refer to FIGS. 3A and 3B: M) of the electrical conductive disc 11 and is connected to the electrical conductive disc 11 in a torsionally rigid manner by means of a flange mounting, welding or adhesion or by means of a further connection means. The electrical conductive disc 11 comprises non-ferromagnetic materials, such as aluminum alloys.

The electrical conductive disc 11 is in operative connection with a second damping element 12, which comprises a plurality of permanent magnets 13. The permanent magnets 13 are arranged on a housing portion of the monochromator 1, arranged concentrically in relation to the longitudinal axis 9 and spaced apart equidistant, for example. Therefore, respective single permanent magnets 13 are fixed statically. In other words, upon rotation of the drive rod 7, the electrical conductive disc 11 rotates in relation to each of the single permanent magnets 13. In general, the above can referred to as a relative movement between both damping elements 11, 12. The permanent magnets 13 are arranged such that magnetic axes 14 thereof are aligned in parallel to the longitudinal axis 9 of the drive rod 7, such that the magnetic fields extend perpendicular to the electrical conductive disc 11.

The installation mentioned above, which comprises the electrical conductive disc 11 and the permanent magnets 13, which are arranged congruent and coplanar in relation to each other, achieves an eddy current brake configured to damp oscillations of the drive rod 7. In general, such oscillations occur due to inertia of moved masses (in particular, in this case, the masses of the drive rod 7 and the optical grating 2) upon finishing rotation or rather rotational positioning of the drive rod 7 by means of the step motor of the drive unit 8. The eddy current brake effect occurred damps this oscillation since energy is absorbed from the oscillation by means of induced eddy currents. Once the electrical conductive disc 11 moves through the magnetic field induced by the permanent magnets 13, eddy currents are induced, which, according to Lenz's law, produce an opposite or rather counter-acting magnetic field. This results in a force oriented opposed to the movement of the electrical conductive disc 11. Hence, increased movement or rather rotational speed of the drive rod 7 results in increased damping force since the braking force is proportional to the relative velocity of the magnetic field and the electrical conductive disc 11 in relation to each other. Hence, advantageously, fast movement results in increased provision of braking force. Decreased electrical resistant of the material of the electrical conductive disc 11 results in increased flow of current which in turn produces strong opposed magnetic forces. Hence, an electrical highly conductive disc 11 can be decelerated in an improved manner. Advantageously, the electrical conductive disc 11 is made of an aluminum alloy. For example, the permanent magnet can be made of a neodymium-iron-boron (NdFeB) magnet.

It is to be noted that the effect of an eddy current brake as shown here is utilized as a damping element rather than in order to brake the drive rod 7. Hence, regular movement of the drive rod 7 is not influenced due to the fact that the installation is free of friction. However, high frequent oscillations are damped as much as possible. As a further advantage, as soon as the step motor of the drive unit 8 stops, the optical grating 2 rapidly stops in a minutely predetermined position, for example a minutely center position within a respective discrete angular range of the step motor of the drive unit 8. In order to prevent intrusion of debris or humidity or rather in order to provide constructional protection of rotating elements, the gap between the electrical conductive disc 11 and the second damping element 12 can be covered (refer to upright lines in FIG. 2).

Figure 3A:
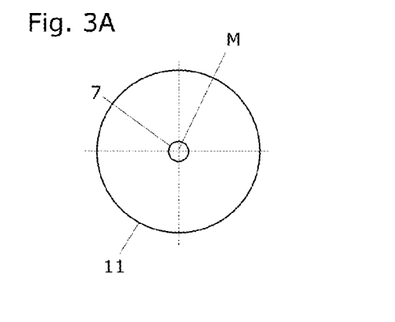
FIG. 3A is a complete circular disc.
Figure 3B:
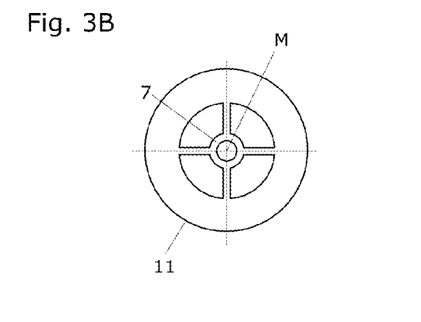
FIG. 3B shows a circular disc, which is recessed sequentially.

FIGS. 3A and 3B show two different exemplary embodiments of the electrical conductive disc 11 of the monochromator 1. The electrical conductive disc 11 depicted in FIG. 3A is a solid disc provided with an opening in the center M thereof in order to allow passage of the drive rod 7 there through. Due to the solid design of the electrical conductive disc 11, induced currents produced inside the electrical conductive disc 11 can be spread in an uninterrupted manner. Hence, the electrical conductive disc 11 can be imparted maximum damping force.

FIG. 3B depicts an electrical conductive disc 11, wherein the inner area thereof comprises cut-out portions. These cut-outs allow reductions in material and therefore reduction of weight. In other words, mass inertia of the electrical conductive disc 11 is reduced. The outer peripheral portion of the disc 11 made of a continuously formed material part and the circumferentially arranged permanent magnets (not shown) of the monochromator 1 are arranged in relation to each other such to be substantially congruent. Hence, the induced currents solely occur in said material part of the disc 11. In comparison to the disc 11 as shown in FIG. 3A, the damping effect of the disc 11 as depicted in FIG. 3B is reduced. However, advantageously, mass inertia of the disc 11 as shown in FIG. 3B is reduced due the weight reduction thereof. Hence, application specific evaluation of the disc 11 design is achieved.

Figure 4A:
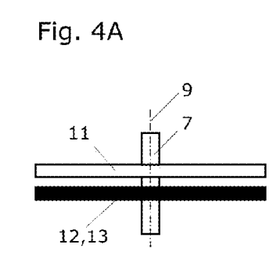
FIG. 4A shows a coplanar arrangement between a first and second damping element, wherein the second damping element is configured by a permanent magnet.

FIGS. 4A to 4G show an overview of different designs and arrangements of the first damping element 11 and the second damping element 12 in relation to each other. In FIG. 4A, the first damping element 11 comprises an electrical conductive disc 11, while the second damping element 12 comprises a magnetic disc having a permanent magnet 13, for example. One of both disc-like damping elements 11, 12 is connected to the drive rod 7 in a torsionally rigid manner, while the other one of the disc-like damping elements 12, 11 is fixed statically, for example fixed to the housing or to the installation of the monochromator 1 (refer to FIGS. 6A and 6B). Therefore, both disc-like damping elements 11, 12 are allowed to rotate in relation to each other. Field lines of the magnetic disc penetrate the electrical conductive disc, which comprises non-ferromagnetic materials. In the course of rotation of both disc-like damping elements 11, 12 in relation to each other, eddy currents are induced inside the electrical conductive disc 11, resulting in generation of an opposed magnetic field, which in turn produces a force which is directed opposed to the relative movement of both disc-like damping elements 11, 12 in relation to each other. Therefore, oscillations of both disc-like damping elements 11, 12 in relation to each other are damped.

Figure 4B:
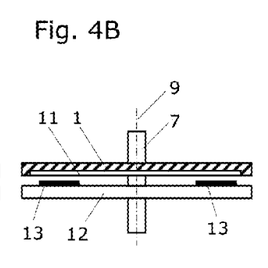
FIG. 4B shows a parallel arrangement between a first damping element and a second damping element comprising a plurality of horizontally oriented permanent magnets.

FIG. 4B depicts an arrangement in which the second damping element 12 comprises a disc, circumferentially equipped with permanent magnets 13 (in the vicinity of the perimeter thereof). Here, the permanent magnets 13 are spaced apart from the longitudinal axis of the drive rod 7 equidistantly. The electrical conductive disc of the disc-like damping element 11 is arranged above the disc-like damping element 12 which is equipped with the permanent magnets 13. In this example, the electrical conductive disc 11 is fixedly introduced into a plate (shown in dashed lines) of the monochromator 1. This arrangement allows a reliable eddy current brake effect in order to damp oscillations of both disc-like damping elements 11, 12 in relation to each other. Similar to the example as shown in FIG. 4A, both disc-like damping elements 11, 12 are rotatable in relation to each other around the longitudinal axis 9.

In an alternative, the plate (shown in dashed lines) of the monochromator 1 can comprise an electrical conductive and non-ferromagnetic material (for example an aluminum alloy), further provided with a recess into which the permanent magnets 13 on the disc 12 are allowed to rotate around the longitudinal axis 9. This recess serves as a cover allowing to prevent entrance of debris or humidity or rather as a constructional protection in order to protect the rotating parts or rather the permanent magnets 13 (refer to upright lines in FIG. 2).

Figure 4C:
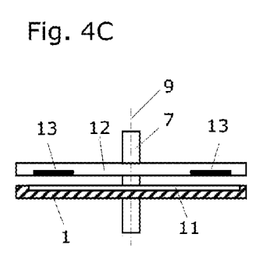
FIG. 4C shows a parallel arrangement between a first damping element comprising a plurality of horizontally oriented permanent magnets and a second damping element.

The example as shown in FIG. 4C relates to an arrangement in which, having regard to the example in FIG. 4B as mentioned above, both disc-like damping elements 11, 12 are arranged in vice-versa. In other words, the disc 12, which is equipped with the permanent magnets 13, is arranged above the electrical conductive disc 11. In this example, the permanent magnets 13 are inserted in respective recesses which are recessed into the disc 12, such that the planes of the permanent magnets 13, which are oriented in the direction of the electrical conductive disc 11, are flush with the plane of the disc 12. It is to be noted that in this example as well as in further examples, both discs 11, 12 can be spaced apart from each other by 0.2 mm to 0.5 mm. The lower this distance is selected, the higher is the achievable damping. Also in this example, as mentioned above, one of the discs 11, 12 is affixed to the drive rod 7 in a torsionally rigid manner, while the other one of the discs 12, 11 is statically affixed.

Figure 4D:
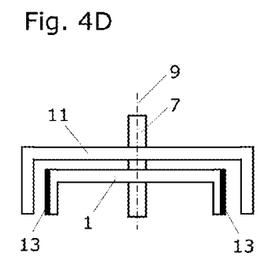
FIG. 4D shows an interlaced arrangement between a first damping element and a second damping element comprising vertically oriented permanent magnets.
Figure 4E:
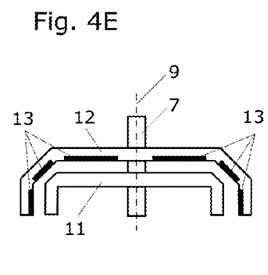
FIG. 4E shows an interlaced arrangement between a first damping element comprising a plurality of vertically oriented, inclined and horizontally oriented permanent magnets and a second damping element.
Figure 4F:
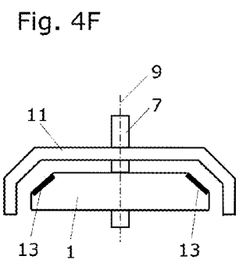
FIG. 4F shows an interlaced arrangement between a first damping element and a second damping element comprising a plurality of inclined permanent magnets.

In the examples as shown in FIGS. 4D-4F, both damping elements 11, 12 are formed essentially to assume a U-shape having different diameters, wherein one of the elements is essentially encompassed by the other one of said elements. This arrangement, as a whole, allows to increase the area portion in which eddy currents are generated inside the electrical conductive damping element 11, which in turn increases the damping action.

In the example shown in FIG. 4D, both damping elements 11, 12 are essentially formed cup-like. The flange portions of the damping element 12, i.e. portions of the damping element 12 which are oriented in parallel to the longitudinal axis 9, are equipped with permanent magnets 13, circumferentially. The magnetic fields of said permanent magnets 13 penetrate into corresponding adjacent flange portions of the electrical conductive damping element 11. One of said damping elements 11, 12 is fixed to the drive rod 7 in a torsionally rigid manner, while the other one of the damping elements 12, 11 is statically affixed. Vibrations or rather oscillations of both damping elements 11, 12 in relation to each other are damped by virtue of the eddy current brake.

In the embodiment shown in FIG. 4E, cup-like damping elements 11, 12 are provided with bending parts or rather folded edges at connection portions to the respective flange portions. This allows provision of increased surface area, which in turn allows a more dense equipment of permanent magnets 13. This results in an increased damping action.

In the example shown in FIG. 4F, the inner portion of the bending part or rather folded edge of the second damping element 12 is equipped with permanent magnets 13. The corresponding outer area of the bending part of the first damping element 11 is aligned to the bending part of the second damping element 12 in parallel. This allows adjustment of application specific damping.

Figure 4G:
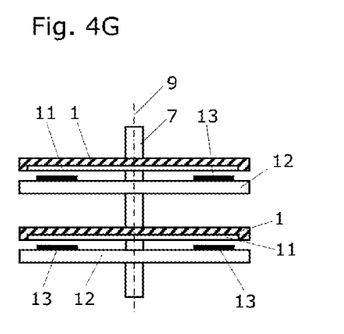
FIG. 4G shows an alternating stacked arrangement comprising two first damping elements and two second damping elements comprising a plurality of horizontally oriented permanent magnets.

FIG. 4G shows an example illustrating two pairs comprising the first and second damping elements, respectively, which are arranged to the drive rod 7 concentrically. The first damping elements 11 comprise an electrical conductive disc, respectively, while the second damping elements 12 comprise a disc, respectively, equipped with a plurality of permanent magnets 13, which are arranged circumferentially. Similar to the example as mentioned above, the electrical conductive discs 12 or the discs 11 equipped with the permanent magnets are connected to the drive rod 7 in a torsionally rigid manner, while the remaining ones of the discs thereof are affixed statically (for example affixed to housing portions). The example as shown in FIG. 4G corresponds to a dual or rather pairwise arrangement of the installation as shown in FIG. 4B. Hence, compared to the arrangement as shown in FIG. 4b, a doubled force for damping the discs 11, 12 in relation to each other is achieved.

Also in this case, the formation of recesses for receiving the permanent magnets (not shown but discussed with respect to FIG. 4B) can be adopted here as well. The recesses serve as cover in order to prevent entrance of debris or humidity or rather to mechanically protect rotating parts or rather the permanent magnets (refer to upright lines in FIG. 2).

Figure 5A:
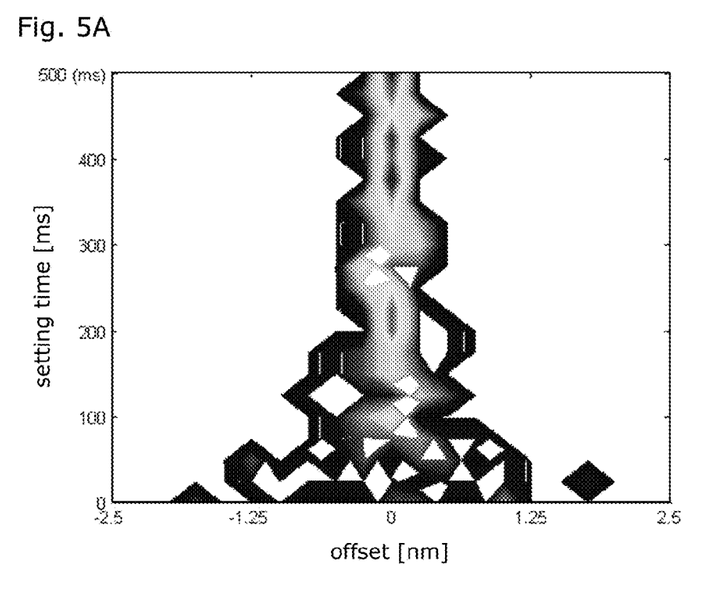
FIG. 5A shows the setting time of a monochromator according to the prior art.
Figure 5B:
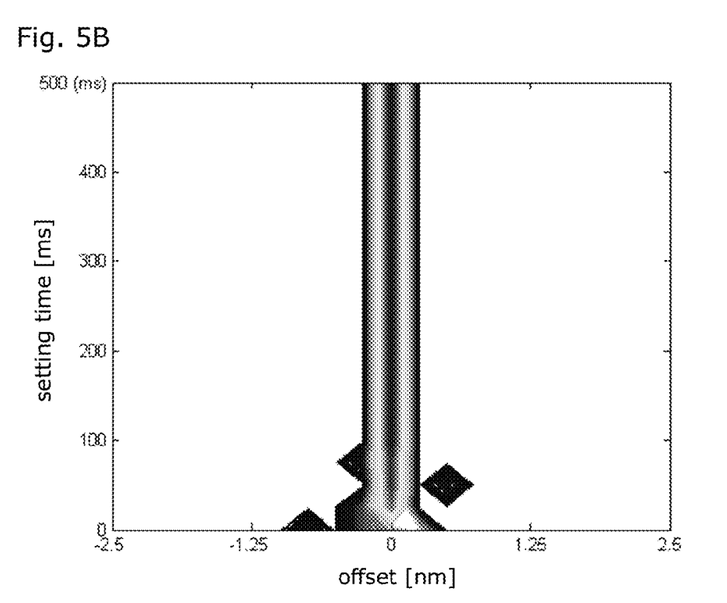
FIG. 5B shows the setting time of the inventive monochromator according to a preferred embodiment.

FIGS. 5A and 5B schematically show a measurement plot depicting a comparison of setting times of a preselected wavelength, based on the measureable wavelength offset, performed by a monochromator according to the prior art (FIG. 5A) and the monochromator 1 according to the present invention (FIG. 5B).

FIG. 5A depicts the setting time of the monochromator according to the prior art. The abscissa represents variation around the point of origin or rather target value of the wavelength (given in nm) impinging the downstream slit diaphragm 5,5' in both directions (+/−), while the ordinate shows the time (given in ms) required for each and every setting. Variations emanating from the point of origin in relation to the setting time upon a wavelength skip of 100 nm are sampled free of any damping. Having regard to the measurement plot, the variation increases with prolonged setting time. For example, the variation is +/−1.25 nm based on a setting time of less than 100 ms. In case of setting times of more than 200 ms the variation is still +/−0.75 nm. While the variation is divided in half, in practical view, this variation, i.e. the variation of the wavelength of the light effectively passing through the downstream slit diaphragm 5, 5', is still too large.

FIG. 5B shows a measurement data plot of wavelength variations in relation to the setting time, which are measured upon a wavelength skip of 100 nm, as well. In the course of these measurements, the optical grating of the monochromator 1 according to the present invention was damped by virtue of the eddy current brake. As shown, the variations of the measurements are reduced impressively as compared to the measurements as sampled in FIG. 5A. Single variations of about +/−0.4 nm to +/−0.75 nm are measured, however solely within the range of very short measurement times of less than 100 ms. Having regard to measurement times of more than 100 ms, variations of merely +/−0.4 nm at maximum are measured throughout. Hence, the essential advantage of the inventive damping action is clearly verified.

In case of a plurality of flashes are averaged in order to achieve maximum precision of an absorption value for each wavelength, the time-saving effect of the measurement of a whole spectrum in small, discrete wavelength steps is especially high. For example, this is true for a range of wavelengths from 200 to 1000 nm, sampled in 1 nm steps, wherein 10 flashes are averaged for each wavelength, respectively. In this case, in an ordinary monochromator, the grating movement takes about 40 ms, respectively, the waiting time period required to wait for settlement (De: Ausschwingen) takes about 250 ms, and the measurement of the 10 flashes (given a flash frequency of 400 Hz) takes about 25 ms. Such measurement is finished in 252 seconds, as a whole. However, the monochromator according to the present invention only requires about 124 seconds due to the fact that the time required for settlement is reduced to 90 ms, for example, assuming similar adjustments. Hence, the waiting time period required to perform a spectral measurement is cut by more than one half.

Figure 6A:
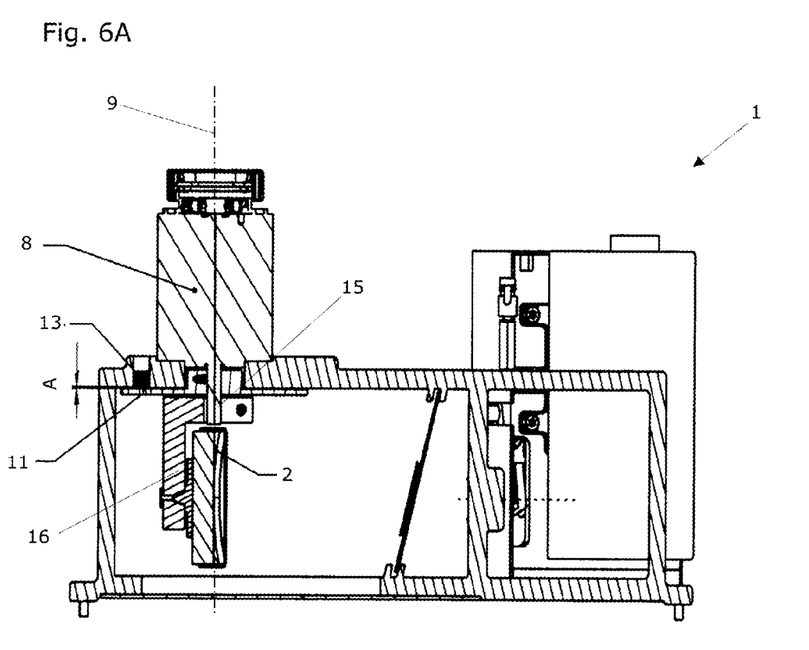
FIG. 6A shows the monochromator in a side sectional view.
Figure 6B:
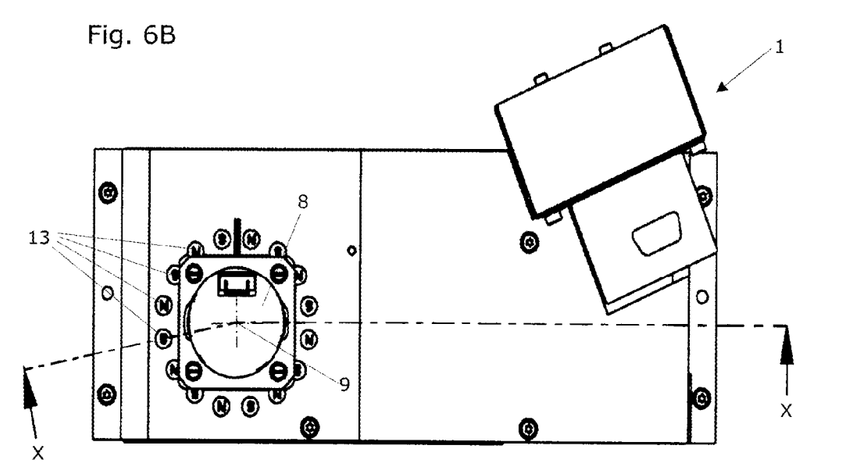
FIG. 6B shows the monochromator in a top view.

FIGS. 6A and 6B show an exemplary assembly of the monochromator 1 according to the present invention, wherein FIG. 6A shows the monochromator 1 in a side sectional view, while FIG. 6B shows the monochromator 1 in a top view. The monochromator 1 as shown in FIG. 6A is cut along a line X-X as depicted in FIG. 6B. The monochromator 1 comprises a drive unit 8 having a step motor which is fixedly mounted to a top housing portion or rather assembly of the monochromator 1 via its housing. A shaft 15 of the step motor or rather drive unit 8 projects in vertical direction trough the housing portion or rather assembly into the housing of the monochromator 1. A support portion 16, which is essentially L-shaped, is flange-mounted or rather connected to a distal portion of the shaft 15 in a torsionally rigid manner. The optical grating 2 is mounted to a portion of the support portion 16 which is oriented in parallel to the longitudinal direction of the shaft 15 or rather longitudinal axis 9. The optical grating 2 is directed such that the plane thereof extends in parallel to the longitudinal direction of the shaft 15. Further, the electrical conductive disc 11 is mounted to the shaft 15 such that the shaft 15 passes through the axial center of the electrical conductive disc 11. Therefore, the outer periphery of the electrical conductive disc 11 is concentrically arranged to the shaft 15 or rather to the longitudinal axis 9. The electrical conductive disc 11 is connected to the shaft 15 in a torsionally rigid manner.

A plurality of permanent magnets 13 are arranged on the top housing portion or rather assembly of the monochromator 1 in an area which is congruent with the electrical conductive disc 11. This feature is shown in more detail in the top view as depicted in FIG. 6B. The permanent magnets 13 are as well arranged in relation to the shaft 15 and the longitudinal axis 9 concentrically and are fixed to the top housing portion or rather assembly of the monochromator 1. For example, the permanent magnets 13 can comprise neodymium-iron-boron (NdFeB) magnets, for example annular magnets having a diameter of 6.0 mm and a length of 5.0 mm. In order to increase damping action, the permanent magnets 13 are arranged such (as shown in FIG. 6B) that permanent magnets 13 adjacent to each other are arranged in opposite polarity.

In order to maximize damping of the permanent magnets 13 and the electrical conductive disc 11 in relation to each other by virtue of the eddy current brake, a distance A between the single permanent magnets 13 and the opposed surface of the electrical conductive disc 11 should be set as small as possible. In order to achieve this, the single permanent magnets 13 are received into and fixed to respective recesses or rather bores in the top housing portion of the monochromator 1.

Upon stopping the step motor of the drive unit 8 subsequent to rotation of the optical grating 2 via the shaft 15 and the support portion 16, oscillations produced on this occasion are damped by virtue of the eddy current brake quickly and reliable. The eddy current brake is formed by the arrangement comprising the electrical conductive disc 11 interacting with the permanent magnets 13. Hence, a transition to different selected wavelengths for performing spectral analysis within the monochromator 1 can be performed quickly and requires less waiting time periods. In addition to said advantages, a very high precision of respective selected wavelength is achieved. Advantageously, the damping is performed free of wear, resulting in further improved precision.

A variety of combinations of disclosed features are encompassed into the scope of the present invention. The same reference numerals in the drawings designate the same or at least similar features, even if they are not described in detail in each case.

Geometrical references made in the description, like upright, vertical, horizontal, refer to the depicted Figures and are not valid in each case. Therefore, elements of the monochromator 1 according to the present invention can be arranged arbitrary in the space as long as general inventive criteria are accomplished as defined in the appended claims.

Further, geometrical definitions like perpendicular or in parallel are meant to be within the precision of manufacturing and can be met more or less precise but can rather be modified as well, such that cone shaped designs can be selected instead of cylindrical assemblies (refer to FIGS. 4D-4F).

| List of reference numerals | |
|---|---|
| 1 | Monochromator |
| 2, 2' | optical grating |
| 3 | source of light |
| 4 | first slit diaphragm |
| 5, 5' | first or rather second downstream slit diaphragm |
| 6 | analyzing apparatus |
| 7, 7' | drive rod |
| 8 | drive unit |
| 9 | longitudinal axis |

-continued

List of reference numerals

| | |
|---|---|
| 10 | control unit |
| 11 | first damping element or rather electrical conductive disc |
| 12 | second damping element or rather disc |
| 13 | permanent magnet, single magnet |
| 14 | magnetic axis |
| 15 | shaft |
| 16 | support portion |
| A | Distance |
| M | center |

The invention claimed is:

1. A monochromator (1), comprising:
at least one optical grating (2) adapted to continuously fan-out incident light of a source of light (3), wherein the optical grating (2) is configured rotatable in order to allow alignment thereof in relation to the incident light;
a drive unit (8) for rotating said optical grating (2);
a drive rod (7) connecting the drive unit (8) to the optical grating (2) for rotating said optical grating (2), wherein the drive rod (7) comprises a longitudinal axis (9), wherein the drive rod (7) and the optical grating (2) are configured rotatable around thereof, and
a control unit (10) for controlling the drive unit (8) and thereby the rotation of the optical grating (2),
wherein the drive unit (8) of the monochromator (1) further comprises:
a first damping element (11) which provides at least one electrical conductive surface, and
a second damping element (12) which provides at least one magnetic field having a magnetic axis (14) which penetrates the electrical conductive surface,
wherein one of the first and second damping elements (11,12) is fixedly connected to the drive rod (7) and is configured rotatable along with the drive rod (7) around the longitudinal axis (9) thereof in relation to the other one of the first and second damping elements (12,11).

2. The monochromator (1) according to claim 1, wherein the magnetic axis (14) of the at least one magnetic field provided by the second damping element (12) extends in parallel to the longitudinal axis (9) of the drive rod (7).

3. The monochromator (1) according to claim 1, wherein the first damping element (11), which provides the electrical conductive surface, is connected fixedly to the drive rod (7), and the second damping element (12) is arranged on a housing of the monochromator (1).

4. The monochromator (1) according to claim 1, wherein the first damping element (11), which provides the electrical conductive surface, comprises a disc (11) which comprises an electrical conductive and non-ferromagnetic material.

5. The monochromator (1) according to claim 1, wherein the first damping element (11) and the second damping element (12) are spaced apart from each other by a distance (A).

6. The monochromator (1) according to claim 1, wherein the second damping element (12) comprises a disc-like magnet.

7. The monochromator (1) according to claim 1, wherein the second damping element (12) comprises at least one single magnet (13) which provides the magnetic field.

8. The monochromator (1) according to claim 7, wherein the second damping element (12) comprises a plurality of single magnets (13), wherein each thereof provides a plurality of magnetic fields, wherein the magnetic axes (14) of all single magnets (13) extend in parallel to the longitudinal axis (9) of the drive rod (7).

9. The monochromator (1) according to claim 7, wherein each single magnet (13) comprises an electric magnet or a permanent magnet (13).

10. The monochromator (1) according to claim 1, wherein the first damping element (11) and the second damping element (12) are formed disc-shaped, respectively.

11. The monochromator (1) according to claim 1, wherein the first damping element (11) and the second damping element (12) are formed identically and are arranged to each other at least partially congruent in the vicinity of the drive rod (7).

12. The monochromator (1) according to claim 1, wherein the first damping element (11) and the second damping element (12) are formed disc-shaped, respectively, and are arranged concentrically in relation to the drive rod (7).

13. The monochromator (1) according to claim 1, wherein the drive unit (8) comprises a step motor.

14. The monochromator (1) according to claim 1, further comprising at least one first downstream slit diaphragm (5) adapted to insulate a particular wavelength of the light fanned-out by the optical grating (2).

15. The monochromator (1) according to claim 1, further comprising at least one second optical grating (2') and a second downstream slit diaphragm (5').

16. The monochromator (1) according to claim 1, wherein:
the drive unit (8) comprises a step motor,
the first damping element (11) comprises an electrical conductive disc comprising a non-ferromagnetic material,
the second damping element (12) comprises a plurality of permanent magnets (13) which are mounted to a housing or rather assembly of the monochromator (1), arranged concentrically in relation to the electrical conductive disc, and wherein each thereof provides a plurality of magnetic fields, wherein the magnetic axes (14) of all permanent magnets (13) extend in parallel to the longitudinal axis (9) of the drive rod (7) and penetrate the electrical conductive disc (11) perpendicularly.

17. The monochromator (1) according to claim 16, wherein the electrical conductive disc (11) comprises aluminum alloy.

18. The monochromator (1) according to claim 16, wherein the permanent magnets (13) and the electrical conductive disc (11) are spaced apart from each other by 0.2 mm to 0.5 mm.

19. A method for using a monochromator (1) according to claim 1, comprising using the monochromator for continuous spectral isolation of a selected wavelength from incident light.

20. A system for measuring at least one of signals selected from a group comprising fluorescence and absorption of samples irradiated with a light from a source of light, comprising at least one monochromator (1) according to claim 1.

* * * * *